(12) United States Patent
Laico

(10) Patent No.: US 10,234,399 B2
(45) Date of Patent: Mar. 19, 2019

(54) APPARATUS AND METHOD FOR OPTICAL INSPECTION OF PARISONS

(71) Applicant: SACMI COOPERATIVA MECCANICI IMOLA SOCIETA' COOPERATIVA, Imola (BO) (IT)

(72) Inventor: Donato Laico, Imola (IT)

(73) Assignee: SACMI COOPERATIVA MECCANICI IMOLA SOCIETA' COOPERATIVA, Imola (IT)

( * ) Notice: Subject to any disclaimer, the term of this patent is extended or adjusted under 35 U.S.C. 154(b) by 0 days.

(21) Appl. No.: 15/562,607

(22) PCT Filed: Apr. 21, 2016

(86) PCT No.: PCT/IB2016/052262
§ 371 (c)(1),
(2) Date: Sep. 28, 2017

(87) PCT Pub. No.: WO2016/170490
PCT Pub. Date: Oct. 27, 2016

(65) Prior Publication Data
US 2018/0088058 A1 Mar. 29, 2018

(30) Foreign Application Priority Data
Apr. 21, 2015 (IT) ................ BO2015A0203

(51) Int. Cl.
*G01N 21/00* (2006.01)
*G01N 21/90* (2006.01)
*B29C 49/02* (2006.01)

(52) U.S. Cl.
CPC ......... *G01N 21/9072* (2013.01); *B29C 49/02* (2013.01); *G01N 21/9045* (2013.01);
(Continued)

(58) Field of Classification Search
CPC ..... B07C 5/3408; B07C 5/122; B07C 5/3422; B65G 2201/0244; B29C 49/02;
(Continued)

(56) References Cited

U.S. PATENT DOCUMENTS

| 4,424,441 A | 1/1984 | Bieringer et al. |
| 5,301,238 A * | 4/1994 | Apter .............. B07C 5/3412 |
| | | 235/462.03 |

(Continued)

FOREIGN PATENT DOCUMENTS

| DE | 102012022474 A1 | 5/2014 |
| EP | 0060918 A1 | 9/1982 |

(Continued)

*Primary Examiner* — Hoa Q Pham
(74) *Attorney, Agent, or Firm* — Pearne & Gordon LLP

(57) ABSTRACT

An apparatus (1) for optical inspection of plastic parisons (2) intended to be blow molded to form containers, comprises a conveyor (3) for transporting corresponding parisons (2) along a predetermined path; at an inspection station along the path, each parison (2) is positioned with its axis (208) aligned with a longitudinal reference axis. A stationary camera (7) is provided, with its viewing axis (8) coincident with the longitudinal reference axis, to view the interior of the parison (2); an illuminator (9) is positioned around the viewing axis (8) of the camera (7), to irradiate the outside surface of a mouth end (202) of the parison (2). The camera (7) has a wide-angle lens, to capture an image of an inside surface of the mouth end (202) of the parison (2), representing a screw thread (205) and the identification code (207) of the parison (2), shown in transparency.

16 Claims, 4 Drawing Sheets

(52) U.S. Cl.
CPC ..... *G01N 21/9054* (2013.01); *G01N 21/9081* (2013.01); *G01N 21/9009* (2013.01)

(58) Field of Classification Search
CPC ............. G01N 21/9054; G01N 21/909; G01N 21/9081; G01N 2033/0081
USPC ....... 356/239.5, 239.4, 240.1, 428; 382/142; 250/223 B, 559.45, 556, 559.42, 559.44
See application file for complete search history.

(56) References Cited

U.S. PATENT DOCUMENTS

| | | | |
|---|---|---|---|
| 5,308,233 A | * | 5/1994 | Denis ................. B29C 49/4215 264/906 |
| 5,510,610 A | * | 4/1996 | Baldwin ............ G01N 21/9045 209/526 |
| 5,926,556 A | * | 7/1999 | Douglas ............. G06K 7/10722 250/223 B |
| 6,878,316 B1 | | 4/2005 | Cochran et al. |
| 7,204,943 B2 | | 4/2007 | Cochran et al. |
| 7,478,660 B2 | * | 1/2009 | Sernesi ................... B65C 9/067 156/362 |
| 2004/0159586 A1 | * | 8/2004 | Dunzinger ............. B29C 49/80 209/11 |
| 2005/0156343 A1 | | 7/2005 | Cochran et al. |
| 2017/0050810 A1 | * | 2/2017 | Tanner ................. B65G 47/846 |

FOREIGN PATENT DOCUMENTS

| | | |
|---|---|---|
| EP | 1674234 A2 | 6/2006 |
| JP | 2009150767 A | 7/2009 |
| JP | 2013159113 A | 8/2013 |
| JP | H5567079 B2 | 8/2014 |
| WO | 2012001414 A2 | 1/2012 |

* cited by examiner

APPARATUS AND METHOD FOR OPTICAL INSPECTION OF PARISONS

TECHNICAL FIELD

This invention relates to an apparatus and a method for optical inspection of parisons.

BACKGROUND ART

A parison is a manufactured article obtained by moulding of thermoplastic material and subjected to a blow moulding process which makes it into a bottle. Typically, the bottle obtained from the parison is intended for the bottling industry, for example to contain alimentary drinks and beverages.

The invention therefore addresses the bottling industry in particular and, more specifically, is applicable to the forming of containers from parisons made of thermoplastic material.

With reference in particular to the bottling industry, a parison is made of plastic material, generally transparent or semitransparent, having an elongate, tubular shape with an open upper part and a lower part constituting a closed bottom.

The parison is characterized by an upper part, called "mouth" or "neck", which is not modified by the blow moulding process and thus remains unchanged in the finished container. The mouth also has on its outside surface a screw thread which differs in diameter and thread type, that is to say, the set of transversal ridges which are formed on its outside surface and which allow a cap to be screwed onto it.

Below the screw thread, the mouth generally has an annular region, called "flange", which is a radially protruding ring.

The lower part of the parison has an elongate structure extending along an axis and tubular in shape. This is the part that is heated and blow moulded to form the container.

Parison moulding machines typically have a plurality of moulds in which the parisons are formed. Typically, a number identifying the mould which has been used to form the parison is stamped (in relief or low relief) on the outside surface of the threaded end of the parison itself.

In the container production process, any parison defects, especially on the threaded portion of the parison, can lead to considerable problems, such as, for example, jamming of the capping machine. This is particularly serious because bottling lines work continuously and their operating speeds (which translates as production capacity) are very high.

Parison inspection apparatuses are therefore known which are designed to check the quality of the parisons by optically analysing the threaded zone.

In this context, it is also useful to know the identification number of the mould used to produce a parison so as to facilitate identification of the cause of a defect and allow prompt action to be taken to eliminate the problem which caused the defect.

Some prior art apparatuses such as, for example, the one described in patent document EP1674234, involve handling the parisons in order to present them to an inspection camera under conditions which are favourable for inspection. In these apparatuses, inspection occurs off line because such handling of the parisons is incompatible with the speed at which the parisons move along the bottling line.

That means, typically, that the quality inspection is carried out only on a sample of the parisons made.

In these cases, typically, the cavity number (representing the mould in which the parison was produced) is derived from an image of an outside surface of the threaded end of the parison.

Another example of an optical inspection apparatus is provided by patent document JP5567079.

In that solution, a plurality of inspection stations operate in temporal succession on the same parison.

This prolongs the time needed for inspection and increases the overall dimensions of the apparatus.

In that solution, the cavity number of the parison is obtained by capturing images of the outside surface of the threaded end of the parison using a camera positioned laterally of the parison itself. This creates a problem of inspection precision if the image is captured with a camera which is stationary and the parison is moving at high speed. In other words, the system is precise only if the parisons are moved at a relatively low speed at the station where the cavity number is detected, which is incompatible with the need to keep in step with the bottling line.

In the solution proposed by JP5567079, there are also other inspection stations with cameras equipped with telecentric lenses designed to look inside the parisons in order to check the bottoms thereof. These stations, however, cannot be used effectively to analyse the screw thread and to read the cavity number.

Thus, the apparatus described in JP5567079, besides being cumbersome and constructionally complex, does not guarantee high performance.

Other examples of optical inspection devices are provided by patent documents DE102012022474A1 and WO2012/001414A2.

DE102012022474A1 describes (in FIGS. 7 and 8) the use of pericentric optical, to see from above the outer side walls of the inspected item (otherwise not visible for perspective reasons).

WO2012/001414A2 describes (FIG. 9) the possibility to top down viewing a preform with a camera 160; this solution has the function to inspect the neck and the bottom of the preform to verify that the colouring of the same is acceptable.

However, such solutions do not allow to read the number of the forming cavity or to effectively inspect the thread; in particular when the preforms move at high speed.

DISCLOSURE OF THE INVENTION

The aim of this invention is to provide an apparatus and a method for optical inspection of parisons to overcome the above mentioned disadvantages of the prior art.

More specifically, the aim of this disclosure is to provide an apparatus and method for optical inspection of parisons allowing inspection to be performed particularly rapidly, also in process, and precisely, with reference in particular to analysis of the screw thread and reading of the cavity number.

A further aim of the disclosure is to provide an apparatus and method for optical inspection of parisons which is constructionally simple and occupies little space.

These aims are fully achieved by the apparatus and method for optical inspection of parison according to the invention as characterized in the appended claims.

More specifically, the apparatus according to this description is an apparatus for optical inspection of parisons made of thermoplastic material. The parisons are intended to be blow moulded to form containers.

The parisons have a cylindrical wall, a closing bottom and a mouth end. The mouth end of the parison has an outside surface and an inside surface. Formed on the outside surface are a screw thread and an identification code in relief or low relief.

The apparatus comprises a conveyor equipped with a plurality of receiving elements configured to transport the parisons individually, and spaced from each other, along a predetermined path.

Along the predetermined path, there is an inspection station where each parison is subjected to optical inspection.

The conveyor is configured to support each parison with its axis aligned with a longitudinal reference axis when the parison is inside the inspection station.

In an embodiment, the conveyor comprises a carousel. In an embodiment, the conveyor comprises a carousel having a plurality of receiving (gripping) elements positioned on its periphery; for example, these receiving elements include recesses formed on the periphery of the carousel. In one example, the carousel is discoidal (a rotating disk).

The apparatus comprises a camera configured to see the interior of the parisons positioned in the inspection station.

The camera is oriented along a viewing axis. The viewing axis coincides with the longitudinal reference axis.

The camera is mounted in a stationary position relative to the conveyor.

The camera is located at a position above the receiving elements of the conveyor when the receiving elements are in transit in the inspection station. More specifically, the camera is located above and oriented towards the mouth end of each of the parisons located in the inspection station in order to see the interior of the parison.

The apparatus also comprises an illuminator to illuminate the parison in the inspection station while the camera captures the image.

The illuminator, too, is in a stationary position relative to the conveyor. The illuminator is located in the inspection station.

Preferably, the illuminator is located around the viewing axis of the camera. More specifically, the illuminator is configured to irradiate the outside surface of the mouth end of the parison positioned in the inspection station.

The camera has a wide-angle lens and is configured to capture, for each parison positioned in the inspection station, an image of an inside surface of the mouth end of the parison positioned in the inspection station.

The captured image represents the screw thread and the identification code of the parison, shown in transparency.

This makes it possible to rapidly inspect the screw thread and the cavity number of each parison. The rapidity is made possible by the fact that a single image is sufficient for each parison and by the fact that each image can be captured precisely even if the parisons are moving along the predetermined path at high speed. It should be noted that, assuming the inspection apparatus is made to work in process, that is to say, in step with the different units of a bottling line, the speed is set by the bottling line. In practice, the captured image comprises a first portion, pertaining to the parison, and a second portion, pertaining to elements positioned outside (around) the parison, which fall within the field of vision of the camera when the image is captured.

The first portion of the image, pertaining to the parison, is circular or substantially circular in shape so that it can be likened to a circle in this description.

Preferably, the conveyor has, at least at the receiving elements, a covering layer made of a material which is opaque and lightly coloured (for example, white) and positioned in such a way that when the parison is in the inspection station, a zone of the conveyor bordering on the parison and directed towards the camera is provided with the covering layer.

In other words, the covering layer of opaque material is applied to all the surfaces of the conveyor which, when any of the receiving elements is positioned in the inspection station to place the corresponding parison with its axis aligned with the viewing axis of the camera, fall within the field of vision of the camera (forming the second portion of the captured image).

This prevents external elements framed in the image but foreign to the parison from spoiling the quality and clarity (for diagnostic purposes) of the image portion pertaining to the parison. The precision and reliability of the inspection is thus increased.

This concept (presence of the covering element) applies, preferably, to all the parts of the apparatus having surfaces which, when a parison is positioned in the inspection station with its axis aligned with the viewing axis of the camera, fall within the field of vision of the camera (forming the second portion of the captured image).

For example, in addition to the receiving and movable transport elements, the conveyor might also comprise a stationary guide located outside the receiving elements along the predetermined path.

According to another aspect of this description, it should be noted that the apparatus comprises computing means, that is, a processing unit (a processor, an electronic card or any other electronic device capable of processing data) connected to the camera to receive and process the image captured by the camera. The purpose of the computing means is to check the screw thread and read the cavity number by analysing the captured image.

Preferably, the computing means are programmed to generate from the captured image a derived image in which an image portion pertaining to the parison is rectangular (instead of circular) in shape. More specifically, in the rectangle forming the first image portion pertaining to the parison in the derived image, two opposite sides of the rectangle correspond to a radius of the circle forming the first image portion pertaining to the same parison in the corresponding captured image.

This facilitates reading of the cavity number and makes subsequent analysis of the quality of the screw thread more effective and precise.

This description thus provides a bottling line equipped with an inspection apparatus operating in process, that is to say, in step with one or more units of the line.

In effect, the conveyor moves continuously, without stopping, and the camera of the inspection apparatus is configured to capture images of the parisons as they move and are positioned one by one in the inspection station.

Preferably, the bottling line comprises a moulding unit for forming parisons from raw plastic by moulding in a plurality of moulds. In this regard, it should be noted that the identification code on the outside surface of the mouth end of each parison indicates (that is, identifies) the mould of the moulding unit in which that parison was formed.

The line may also comprise a thermal conditioning unit designed to receive the parisons from the parison moulding unit (either directly or through a parison storage unit).

The line may also comprise a unit for blow moulding the parisons into respective containers and positioned downstream of the thermal conditioning unit, and other units, such as, for example, a filling unit, a capping unit and a labelling unit.

In this context, it should be noted that the conveyor of the inspection apparatus preferably moves in step with the thermal conditioning unit.

The conveyor of the inspection apparatus might also coincide with one of the conveyors of the other units of the line. Alternatively, the conveyor might be constituted (that is, defined by) a transfer unit by which the parisons are transferred from one unit to another of the line (for example, a transfer unit interposed between the parison moulding unit and the thermal conditioning unit, or a transfer unit interposed between the thermal conditioning unit and the blow moulding unit).

This description also provides a method for optical inspection of parisons intended to be blow moulded to form containers.

The method comprises a step of moving the parisons along a predetermined path by means of a conveyor to feed the parisons into (and out of) an inspection station (that is, an inspection zone) in which each parison is positioned with its axis aligned with a longitudinal reference axis.

For each parison positioned in the inspection station, a (preferably single) image is captured by a camera. The viewing axis of the camera preferably coincides with the longitudinal reference axis. The camera is mounted in a stationary position relative to the conveyor, above the mouth end of each of the parisons located in the inspection station in order to see the interior of the parison.

During the step of capturing each image, the method comprises a step of illuminating the parison positioned in the inspection station by directing light rays at the outside surface of the mouth end of the parison A wide-angle lens is used to capture, for each parison, an image of an inside surface of the mouth end of the parison, representing the screw thread and the identification code of the parison, shown in transparency.

Preferably, when the parison is in the inspection station (and this applies to each parison) one end of the camera is positioned at a distance of a few dozen millimeters from the parison. This distance is preferably less than 90 mm. For example, this distance is included in the interval 20-70 millimeters.

Preferably, a surface of the conveyor framed in the image captured by the camera is provided with a covering layer made of an opaque, light-coloured material.

Preferably, the method also comprises a step of processing the images captured by the camera to obtain corresponding derived images. In the captured image, the (first) image portion pertaining to the parison has the shape of a circle. In the derived image, the image portion pertaining to the parison has the shape of a rectangle where two opposite sides of the rectangle correspond to a radius of the circle.

BRIEF DESCRIPTION OF DRAWINGS

This and other features of the disclosure will become more apparent from the following detailed description of a preferred, non-limiting example embodiment of it, with reference to the accompanying drawings, in which.

DETAILED DESCRIPTION OF PREFERRED EMBODIMENTS OF THE INVENTION

Figure 1:
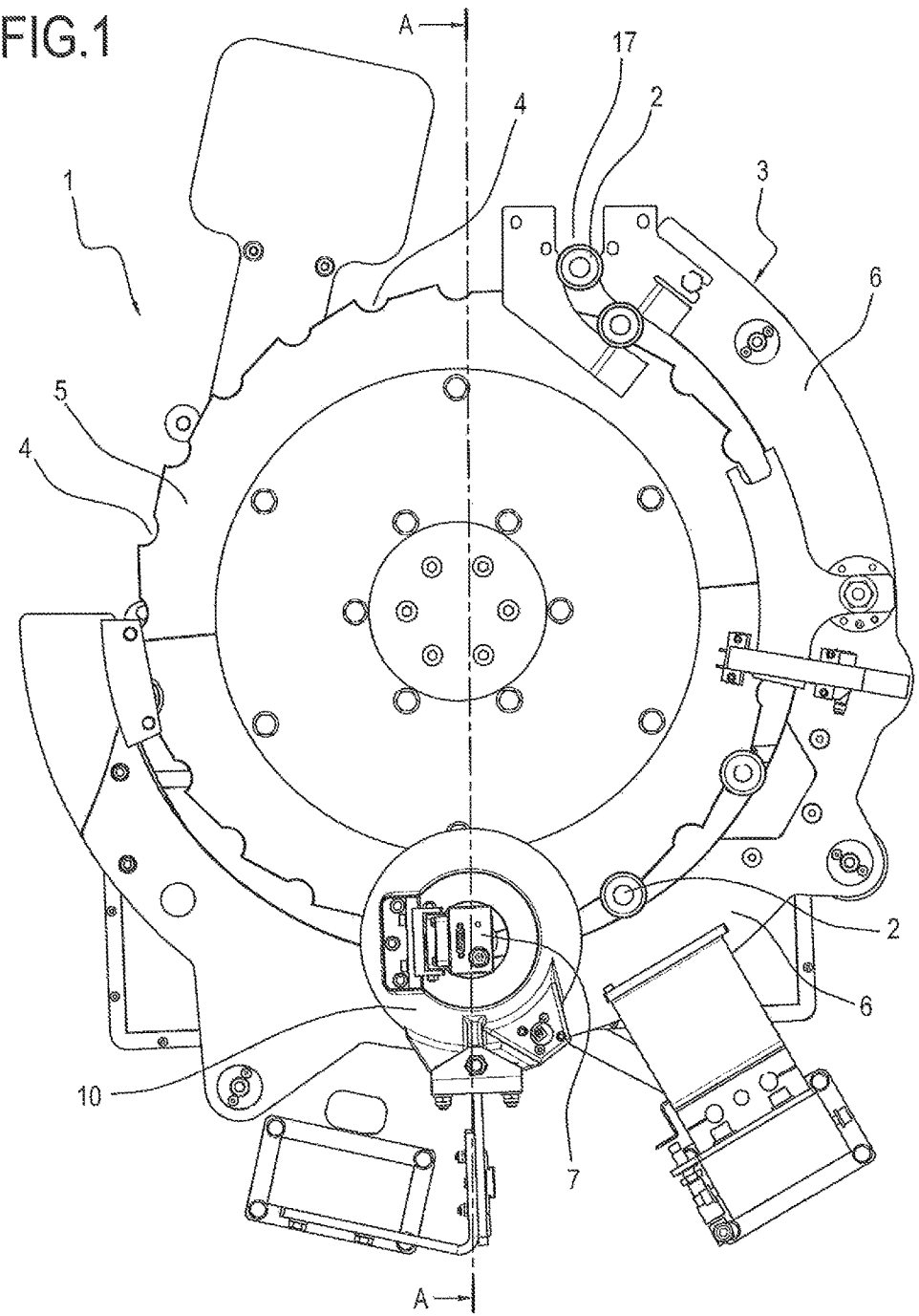
FIG. 1 is a plan view of an inspection apparatus according to this disclosure.
Figure 2:
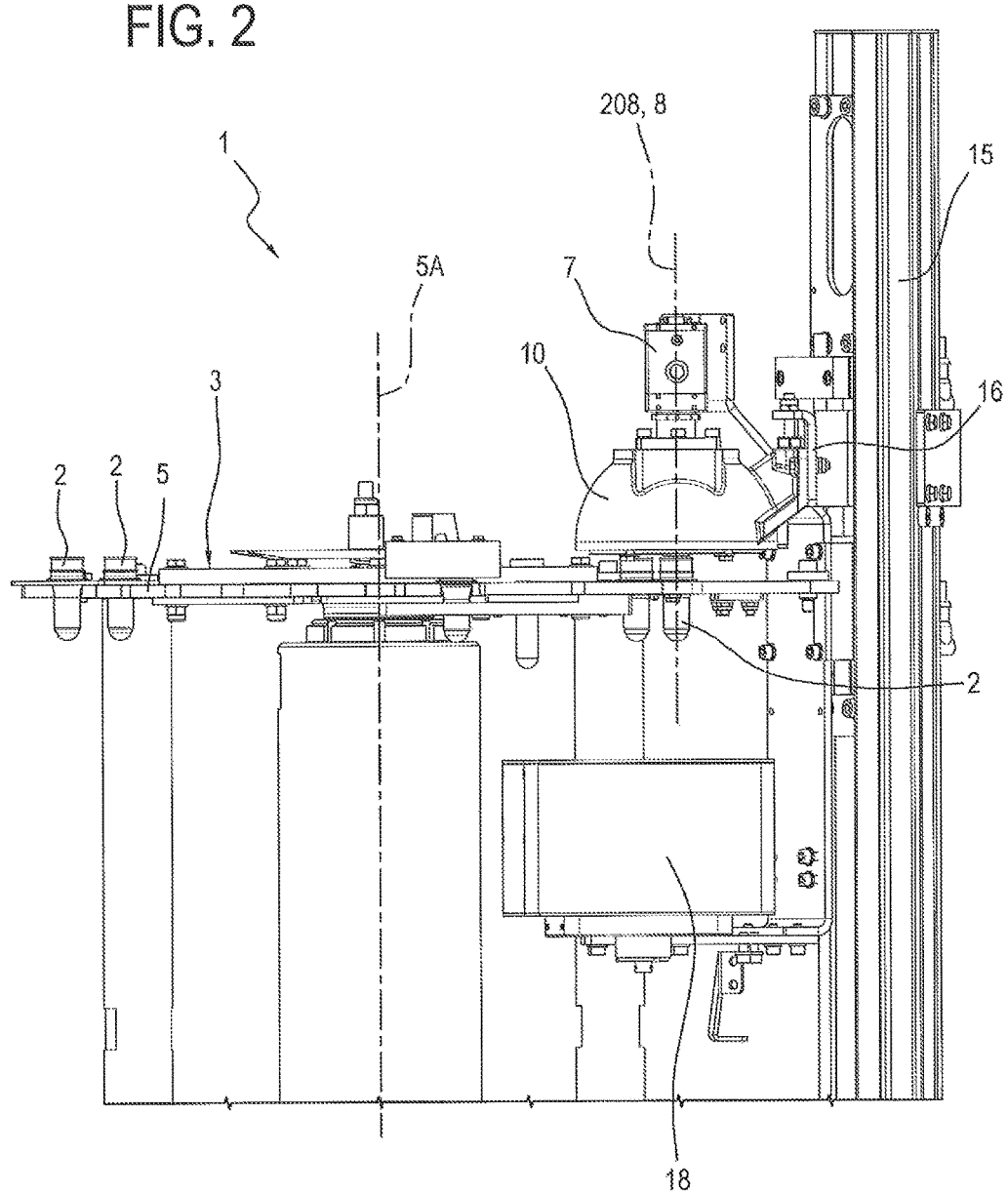
FIG. 2 illustrates the apparatus of FIG. 1 in a side view.
Figure 4:
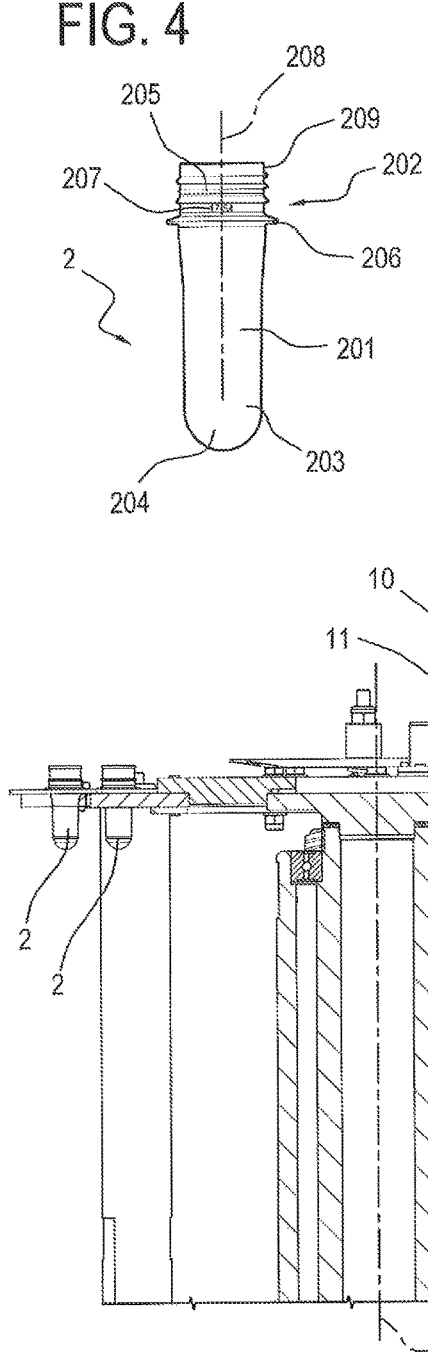
FIG. 4 illustrates an example of a parison.
Figure 3:
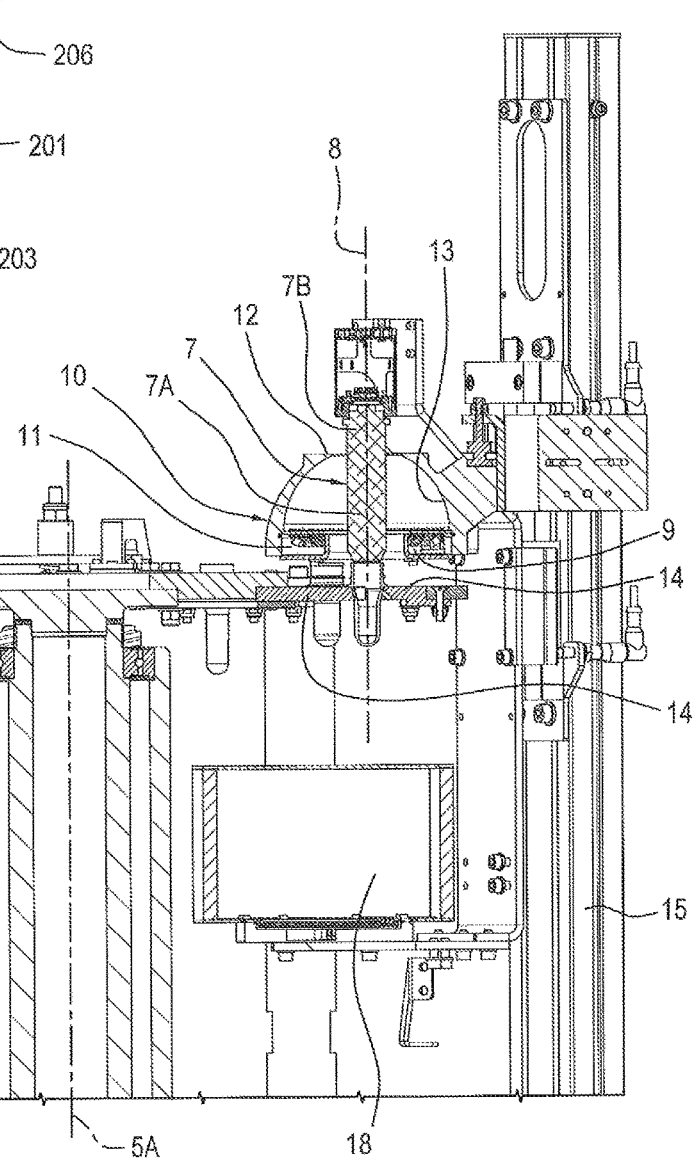
FIG. 3 illustrates the apparatus of FIG. 1 in a cross sectional view through the section plane labelled A-A in FIG. 1.
Figure 5:
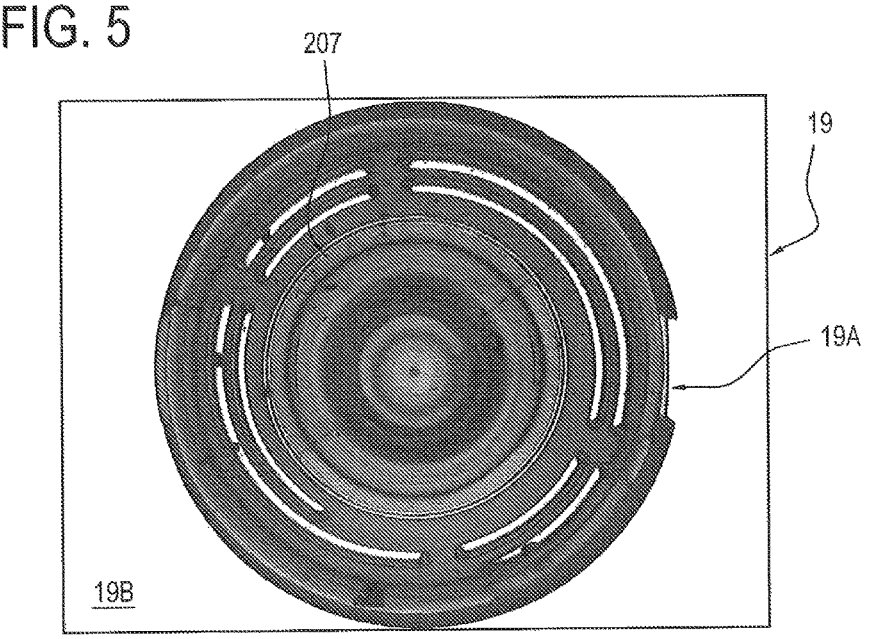
FIG. 5 illustrates an example of an image captured by the inspection apparatus according to this description.
Figure 6:
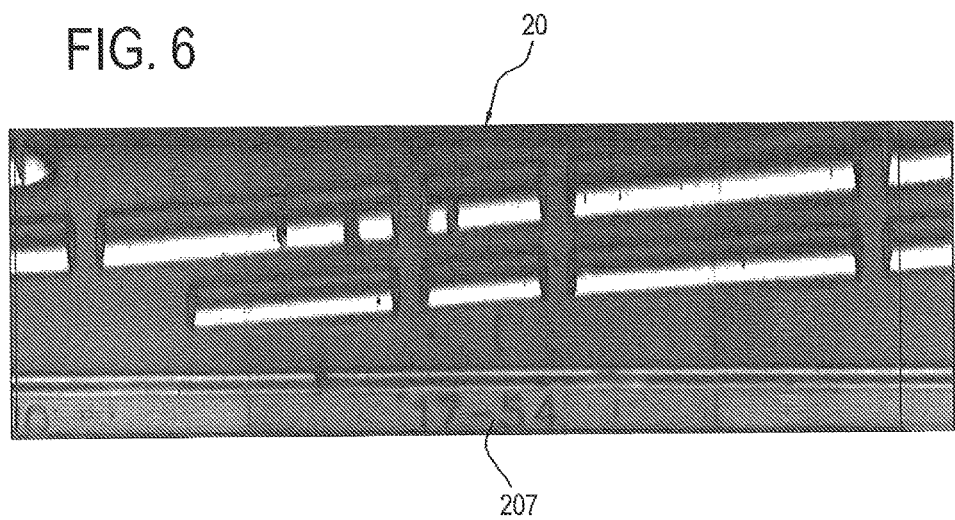
FIG. 6 illustrates an example of an image derived by the apparatus of FIG. 1 from the image of FIG. 5.

In the drawings, the numeral 1 denotes an apparatus for optical inspection of parisons 2. The parisons 2 are configured to be blow moulded to form containers according to technology which is known in the bottling industry.

The parisons are made of a plastic material (for example, PET) and are generally transparent or semitransparent.

The parison 2 has a cylindrical or substantially cylindrical side wall 201. The side wall 201 has a first end 202 which is open and a second end 203 which is closed by a bottom wall 204 (or bottom).

The first end 202 defines a mouth of the parison 2 and will hereinafter be referred to as "mouth end" of the parison 2.

The mouth end 202 has an inside (cylindrical or substantially cylindrical) surface and an outside (cylindrical or substantially cylindrical) surface.

The outside surface of the mouth end 202 has a screw thread 205.

Some types of parisons 2 are provided with an annular protrusion 206, called flange, located in a zone of transition between the side wall 201, which is not threaded, and the mouth end 202, which is provided with the screw thread 205.

Stamped in low relief on the outside surface of the mouth end 202 is a numeric or alphanumeric identification code 207. The identification code 207 corresponds to and identifies the mould which produced, that is, moulded, the parison 2 itself during a process for moulding the parisons 2. In this description, the identification code is also referred to as "cavity number".

The parison 2 is cylindrical in shape and extends along an axis 208 defined by this shape.

The mouth end 202 also has an annular rim 209 which defines a reference plane (passing through a circle defined by the annular rim 209). The reference plane is transversal, that is, perpendicular, to the axis 208 of the parison 2.

The apparatus 1 comprises a conveyor 3 designed to transport the parisons 2 along a predetermined path. Preferably, the parisons 2 are transported by the conveyor 3 along at least one stretch of the predetermined path, individually and spaced from each other. Preferably, the parisons 2 transported by the conveyor 3 along the at least one stretch of the predetermined path are equally spaced from each other at a predetermined spacing (which, if necessary, is variable and adjustable as a function of the speed of the conveyor 3).

The conveyor 3 has a plurality of receiving elements 4. The receiving elements 4 are configured to receive (support) and then transport corresponding parisons 2 along the predetermined path.

Each receiving element 4 is preferably shaped in such a way as to define a receiving axis so that when a parison 2 is coupled to the receiving element 4, the axis 208 of the parison 2 is aligned with, that is, coincides with, the receiving axis of the receiving element 4 itself.

In one example embodiment, the conveyor 3 is rotary and rotates about an axis of rotation 5A. More specifically, in the example illustrated, the conveyor 3 has a disc-shaped carousel 5 and the receiving elements 4 are recesses formed on a periphery of the carousel 5. Further, outside at least one stretch of the periphery of the carousel 5, there is a stationary guide 6 on which the parisons 2 coupled to the receiving elements 4 of the carousel 5 rest (sliding or rolling). In practice, the guide 6 forms part of the conveyor (which means that in this embodiment, the conveyor 3 actually has a movable part and a stationary part).

It should be noted that the conveyor might be made in any of a variety of possible (alternative) forms. For example, it might have a belt or a chain and a plurality of arms connected to the chain and equipped with grippers or other means for receiving the parisons.

Along the predetermined path followed by the parisons 2, there is an inspection station (or zone). As they move along the predetermined path, the parisons 2 pass through the inspection station along a stretch of the predetermined path.

The conveyor 3 is structured in such a way that the receiving axes of the receiving elements 4 are parallel to a longitudinal reference axis (stationary) along the stretch of the predetermined path located at the inspection station and at at least one position along the predetermined path, so that the receiving axes of the receiving elements 4 are aligned with, that is, coincide with, the longitudinal reference axis.

Thus, the conveyor 3 is structured in such a way as to support the parisons 2, in the inspection station, with the reference plane of the parisons 2 themselves perpendicular to the longitudinal reference axis.

Preferably (but not necessarily), the predetermined path is planar, that is to say, it is contained in one plane. The plane is parallel to the reference plane of the parisons 2 transported by the conveyor 3. Preferably, therefore, the conveyor 3 is structured in such a way that the parisons 2 keep their reference plane perpendicular to the longitudinal reference axis at all times during their movement along the predetermined path.

The apparatus also comprises a camera 7 configured to see the parisons 2 positioned in the inspection station.

The camera 7 defines its own viewing axis 8. The viewing axis 8 of the camera 7 coincides with the longitudinal reference axis.

The camera 7 is in a stationary position relative to the conveyor 3, that is, relative to the movement of the parisons.

The camera 7 is at a position above the parisons 2 which, in the inspection station, are aligned with the viewing axis 8 of the camera 7 itself.

In the inspection station, the parisons 2 are oriented with the mouth end 202 directed towards the camera 7. In other words, the camera 7 is directed towards the mouth of the parisons 2 positioned in the inspection station, so as to see the interior of the parisons 2.

The apparatus 1 also comprises an illuminator 9 mounted in a stationary position.

the illuminator 9 is located around the viewing axis 8 of the camera 7. The illuminator 9 is configured to irradiate the outside surface of the mouth end 202 of the parison 2 positioned in the inspection station.

The camera 7 has a wide-angle lens. Preferably, the camera lens has an aperture of 90 sexagesimal degrees. Preferably, the camera lens is of the type known as "pinhole lens".

The camera 7 is configured to capture, for each parison 2 positioned in the inspection station, an image 19 representing the interior of the parison 2. More specifically, the image 19 captured by the camera 7 represents the inside surface of the mouth end 202 of the parison 2 (positioned in the inspection station).

The captured image contains a circular figure in which an annular zone (shaped like a circular crown) represents the screw thread and the identification code of the parison. It should be noted that the screw thread and the identification code 207 are shown in transparency. The circular figure forms a first portion 19A of the captured image 19. The captured image 19 also comprises a second portion 19B located outside the first portion 19A.

In one example embodiment, the apparatus 1 comprises a shell 10, that is, a hollow element, located in the inspection station in a stationary position. The shell 10 has an annular rim defining a housing 11 for the illuminator 9. The shell 10 also has a bottom 12. The shell 10 also has a concave wall 13 joining the bottom 12 to the annular rim of the shell 10 itself.

The shell 10 is positioned around the camera 7. Preferably, the camera 7 has at least a first part 7A positioned inside the shell and surrounded by the concave wall 13. This allows one end of the camera to be directed towards the parisons 2 at a minimum distance (for example, a few dozen millimeters) from the parisons 2.

In an example embodiment, the bottom 12 of the shell 10 has a through hole in it. Preferably, the camera 7 is mounted so it passes through the hole in the bottom 12, with its second part 7B located outside the shell 10. Preferably, one end of the camera 7 directed towards the conveyor 3, that is, towards the parison 2 positioned in the inspection station, is surrounded by the annular rim of the shell 10.

Preferably, one end of the camera 7 directed towards the conveyor 3, that is, towards the parison 2 positioned in the inspection station, is surrounded by the illuminator 9.

Preferably, the illuminator 9 has the shape of a ring. For example, the illuminator has a plurality of illuminating elements (for example LEDs) arranged in a ring and oriented in such a way as to project rays which converge towards the camera viewing axis, inclined thereto at an angle included in the interval [20-60] sexagesimal degrees.

Preferably, the conveyor 3 has a covering layer 14 at least at the receiving elements 4.

The covering layer 14 is made of an opaque material, which does not reflect light. Preferably, the covering layer 14 is made of a light-coloured material, for example white or light grey.

The covering layer 14 is positioned at the receiving elements 4 in such a way that when each parison 2 is in the inspection station, a zone of the conveyor bordering on the parison 2 and directed towards the camera 7 is provided with the covering layer 14.

In the example illustrated, where the conveyor 3 has a disc-shaped carousel with a plurality of recesses formed on its periphery to house corresponding parisons (and thereby defining the receiving elements 4) and a stationary guide 6 surrounding at least one stretch of the carousel 5, the covering layer 14 is applied to at least one portion of the guide 6 and to at least one portion of the carousel 5 surrounding the recesses.

Preferably, the covering layer 14 is made from one or more replaceable plates.

The apparatus 1 preferably also comprises a back illuminator 18, mounted in such a way as to direct light rays towards the bottom wall 204 of the parison 2 positioned inside the inspection station. In practice, the back illuminator 18 is oriented in a direction substantially opposite to the illuminator 9 and to the camera 7. The parison 2 positioned in the inspection station is interposed, along the longitudinal reference axis, between the camera 7 and the illuminator 9, which are proximal to the mouth end 202 of the parison, and the back illuminator 18, which is proximal to the second end 203 of the parison 2.

The back illuminator 18 improves the quality of the captured image 19 for the purposes of subsequent processing.

Preferably, the apparatus 1 has a column 15 and a carrier 16 movably coupled to the column 15 in such a way as to move along an axis parallel to the viewing axis 8 of the camera 7.

The carrier 16 comprises the camera 7. The carrier 16 preferably also comprises the illuminator 9 and, preferably, the shell 10.

The apparatus 1 comprises a control unit. The control unit comprises a processor, embodied by an electronic card, or computing means or other electronic appliances of essentially known type.

The control unit is connected to the camera 7 to conduct image capturing operations. The control unit is also preferably connected to the illuminator 9 in order to drive it. Preferably, the control unit is programmed to drive the illuminator 9 stroboscopically in such a way that the illuminator 9 is lit each time a parison is inside the inspection station and switches on and off alternately.

The control unit also drives the camera 7 in such a way that it captures an image each time the axis 208 of a parison 2 is aligned with the viewing axis 8 of the camera 7 (the two axes, at that instant, coinciding with the longitudinal reference axis).

Preferably, the apparatus 1 comprises computing means (forming part of the control unit or separate therefrom).

The computing means (programmed DSP, processor, electronic card or other) are connected to the camera 7 to receive the images captured by it and process them).

In each image 19 captured by the camera 7 there is a first image portion 19A pertaining to the parison 2. This image portion has the shape of a circle.

The computing means are programmed to generate from the captured image a derived image 20 having at least one image portion pertaining to the parison and having the shape of a rectangle. In such case, preferably, two opposite sides of the rectangle correspond to a radius of the circle.

Thus, the rectangle is a linear development of the circle (in the same way as an upper or lower half of a planisphere is a linear development of a hemispherical surface of the Earth captured in a two-dimensional image).

There is a step of calibrating the camera 7 in which the camera captures an image of an element of known shape and geometry, in order to store information representing a distortion of the captured image.

The computing means are programmed to process the captured image and (based on the calibration information) to compensate or reduce a distortion effect on the captured image due to the use of a wide-angle lens in the camera 7.

It should be noted that the conveyor 3 preferably moves continuously, without stopping. The camera 7 is configured to capture images of the parisons 2 as they move and are positioned one by one in the inspection station.

Operatively, the apparatus 1 works as follows.

The parisons are loaded by the conveyor 3 into an infeed or loading station 17.

Each parison 2 is transported individually into the stationary inspection station where, at a certain instant, it is located with its axis 208 aligned with the viewing axis 8 of the camera 7. In that position, the annular rim 209 is at a minimum distance from the camera 7 (in practice, it skims the camera).

In that position, the parison is illuminated by irradiation on the outside surface of the parison 2 itself and the camera captures an image 19 of the interior of the parison 2, with reference in particular to the inside surface of the mouth end 202 of the parison 2. The captured image represents the screw thread and the identification code of the parison, which are shown in transparency and with back lighting.

Further, each captured image is processed to generate a derived image 20.

More specifically, a first portion 19A of the captured image 19, which first portion pertains to the parison 2 and has the shape of a circle, is processed by a linearization process so that the derived image 20 comprises a rectangle corresponding to that circle.

According to another aspect of this description, a bottling line is provided which comprises the device 1 having one or more of the features described above.

For example, the bottling line (whose parts other than the inspection apparatus 1 are not illustrated) comprises a moulding unit for forming parisons from raw plastic by moulding in a plurality of moulds.

The bottling line also comprises a thermal conditioning unit, located downstream of the parison moulding unit, for continuously receiving the parisons from the parison moulding unit and feeding them to a blow moulding machine configured to produce containers from the parisons.

The inspection apparatus 1 is installed in the line in step with the other units of the line.

More specifically, the conveyor 3 of the inspection apparatus 1 is in step with the thermal conditioning unit More specifically, the conveyor 3 of the inspection apparatus 1 is in step with the moulding unit for forming the parisons 2.

The invention claimed is:

1. An apparatus for optical inspection of parisons intended to be blow moulded to form containers, wherein the parisons are made of plastic material and have a side wall, a closing bottom and a mouth end, the mouth end having on its outside surface a screw thread and an identification code in relief, wherein the apparatus comprises:
   a conveyor equipped with a plurality of receiving elements configured to transport corresponding parisons along a predetermined path, wherein, in an inspection station located along the predetermined path, each parison is positioned with its axis aligned with a longitudinal reference axis;
   a camera having a viewing axis coinciding with the longitudinal reference axis and located in a stationary position relative to the conveyor, above the mouth end of each of the parisons located in the inspection station, in order to see the interior of the parison;
   an illuminator positioned around the viewing axis of the camera and configured to irradiate the outside surface of the mouth end of the parison positioned in the inspection station,
wherein the camera has a wide-angle lens and is configured to capture an image of an inside surface of the mouth end of the parison positioned in the inspection station, said image being representative of the screw thread and of the identification code of the parison, shown in transparency,
and wherein the conveyor has, at least at the receiving elements, a covering layer made of an opaque, light-coloured material and positioned in such a way that when each parison is in the inspection station, a zone of the conveyor bordering on the parison and directed towards the camera is provided with the covering layer.

2. The apparatus according to claim 1, wherein the lens of the camera has an aperture of 90 sexagesimal degrees.

3. The apparatus according to claim 1, wherein the conveyor comprises:

a disc-shaped carousel rotating about a longitudinal axis and having a plurality of recesses formed on its periphery to house corresponding parisons;

a stationary guide surrounding at least one stretch of the carousel, to define a supporting and rolling surface for the parisons coupled to the carousel, wherein at least one portion of the guide and one portion of the carousel surrounding the recesses are provided with a covering layer, and wherein the apparatus comprises a back illuminator opposite to the camera to produce light beams directed towards the camera, wherein the parisons operatively positioned in the inspection station are operatively interposed along the viewing axis between the camera and the back illuminator.

4. The apparatus according to claim 1, comprising a control unit connected to the camera and to the illuminator to drive the illuminator stroboscopically so that the illuminator is lit and the camera captures an image each time a parison is in the inspection station.

5. The apparatus according to claim 1, comprising processing unit which are connected to the camera to receive from the camera a captured image in which a first image portion pertaining to the parison has the shape of a circle and which is programmed to process the captured image to generate a derived image having at least one portion pertaining to the parison and having the shape of a rectangle where two opposite sides of the rectangle correspond to a radius of the circle of the first portion of the captured image.

6. The apparatus according to claim 1, wherein the conveyor moves continuously, without stopping, so that the camera is configured to capture images of the parisons as they move and are positioned one by one in the inspection station.

7. A bottling line comprising:
a moulding unit for forming parisons from raw plastic by moulding in a plurality of moulds, where the parisons have a side wall, a closing bottom and a mouth end, the mouth end having on its outside surface a screw thread and an identification code identifying the mould in which that parison was formed;
an apparatus for optical inspection of the parisons,
wherein the inspection apparatus is an inspection apparatus according to claim 1.

8. The bottling line according to claim 7, comprising a thermal conditioning unit, located downstream of the parison moulding unit, for continuously receiving the parisons and feeding them to a blow moulding machine configured to produce containers from the parisons, wherein the conveyor of the inspection apparatus is in step with the thermal conditioning unit.

9. An apparatus for optical inspection of parisons intended to be blow moulded to form containers, wherein the parisons are made of plastic material and have a side wall, a closing bottom and a mouth end, the mouth end having on its outside surface a screw thread and an identification code in relief, wherein the apparatus comprises:
a conveyor equipped with a plurality of receiving elements configured to transport corresponding parisons along a predetermined path, wherein, in an inspection station located along the predetermined path, each parison is positioned with its axis aligned with a longitudinal reference axis;
a camera having a viewing axis coinciding with the longitudinal reference axis and located in a stationary position relative to the conveyor, above the mouth end of each of the parisons located in the inspection station, in order to see the interior of the parison;

an illuminator positioned around the viewing axis of the camera and configured to irradiate the outside surface of the mouth end of the parison positioned in the inspection station, wherein the camera has a wide-angle lens and is configured to capture an image of an inside surface of the mouth end of the parison positioned in the inspection station, said image being representative of the screw thread and of the identification code of the parison, shown in transparency,
wherein the apparatus further comprises a shell including:
an annular rim defining a housing for the illuminator;
a bottom;
a concave wall joining the bottom to the annular rim,
wherein the camera has at least a first part positioned inside the shell and surrounded by the concave wall.

10. The apparatus according to claim 9, wherein the bottom of the shell has a through hole through which the camera is mounted with its second part positioned outside the shell.

11. The apparatus according to claim 9, wherein one end of the camera directed towards the conveyor is surrounded by the annular rim of the shell.

12. A bottling line comprising:
a moulding unit for forming parisons from raw plastic by moulding in a plurality of moulds, where the parisons have a side wall, a closing bottom and a mouth end, the mouth end having on its outside surface a screw thread and an identification code identifying the mould in which that parison was formed;
an apparatus for optical inspection of the parisons,
wherein the inspection apparatus is an inspection apparatus according to claim 9.

13. A method for optical inspection of parisons intended to be blow moulded to form containers, where the parisons are made of plastic material and have a side wall, a closing bottom and a mouth end, the mouth end having on its outside surface a screw thread and an identification code in relief, wherein the method comprises the following steps:
moving the parisons along a predetermined path by means of a conveyor to feed the parisons into an inspection station in which each parison is positioned with its axis aligned with a longitudinal reference axis;
capturing an image, for each parison positioned in the inspection station, by means of a camera having a viewing axis coinciding with the longitudinal reference axis and located in a stationary position relative to the conveyor, above the mouth end of each of the parisons located in the inspection station in order to see the interior of the parison;
illuminating each parison positioned in the inspection station by directing light rays at the outside surface of the mouth end of the parison,
wherein the capturing step is performed with a wide-angle lens in order to capture, for each parison, an image of an inside surface of the mouth end of the parison, representing the screw thread and the identification code of the parison, shown in transparency,
wherein the conveyor includes a covering layer, the covering layer being made of an opaque, light-coloured material and being positioned in such a way that, when each parison is in the inspection station, a zone of the conveyor bordering on the parison and directed towards the camera is provided with the covering layer.

14. The method according to claim 13, comprising a step of processing the images captured by the camera to obtain corresponding derived images, wherein, in the captured image, a first image portion pertaining to the parison has the shape of a circle and, in the corresponding derived image, the image portion pertaining to the parison has the shape of a rectangle, wherein two opposite sides of the rectangle correspond to a radius of the circle.

15. A method for optical inspection of parisons intended to be blow moulded to form containers, where the parisons are made of plastic material and have a side wall, a closing bottom and a mouth end, the mouth end having on its outside surface a screw thread and an identification code in relief, wherein the method comprises the following steps:

moving the parisons along a predetermined path by means of a conveyor to feed the parisons into an inspection station in which each parison is positioned with its axis aligned with a longitudinal reference axis;

capturing an image, for each parison positioned in the inspection station, by means of a camera having a viewing axis coinciding with the longitudinal reference axis and located in a stationary position relative to the conveyor, above the mouth end of each of the parisons located in the inspection station in order to see the interior of the parison;

illuminating each parison positioned in the inspection station by directing light rays at the outside surface of the mouth end of the parison, wherein the capturing step is performed with a wide-angle lens in order to capture, for each parison, an image of an inside surface of the mouth end of the parison, representing the screw thread and the identification code of the parison, shown in transparency, wherein, for each parison, when the parison is in the inspection station, one end of the camera is positioned at a distance of less than 90 mm from the parison, and wherein a surface of the conveyor framed in the image captured by the camera is provided with a covering layer made of an opaque, light-coloured material.

16. The method according to claim 15, comprising a step of processing the images captured by the camera to obtain corresponding derived images, wherein, in the captured image, a first image portion pertaining to the parison has the shape of a circle and, in the corresponding derived image, the image portion pertaining to the parison has the shape of a rectangle, wherein two opposite sides of the rectangle correspond to a radius of the circle.

* * * * *